Sept. 29, 1942. L. NEWMAN Plant Pat. 545
ROSE PLANT
Filed Dec. 22, 1941
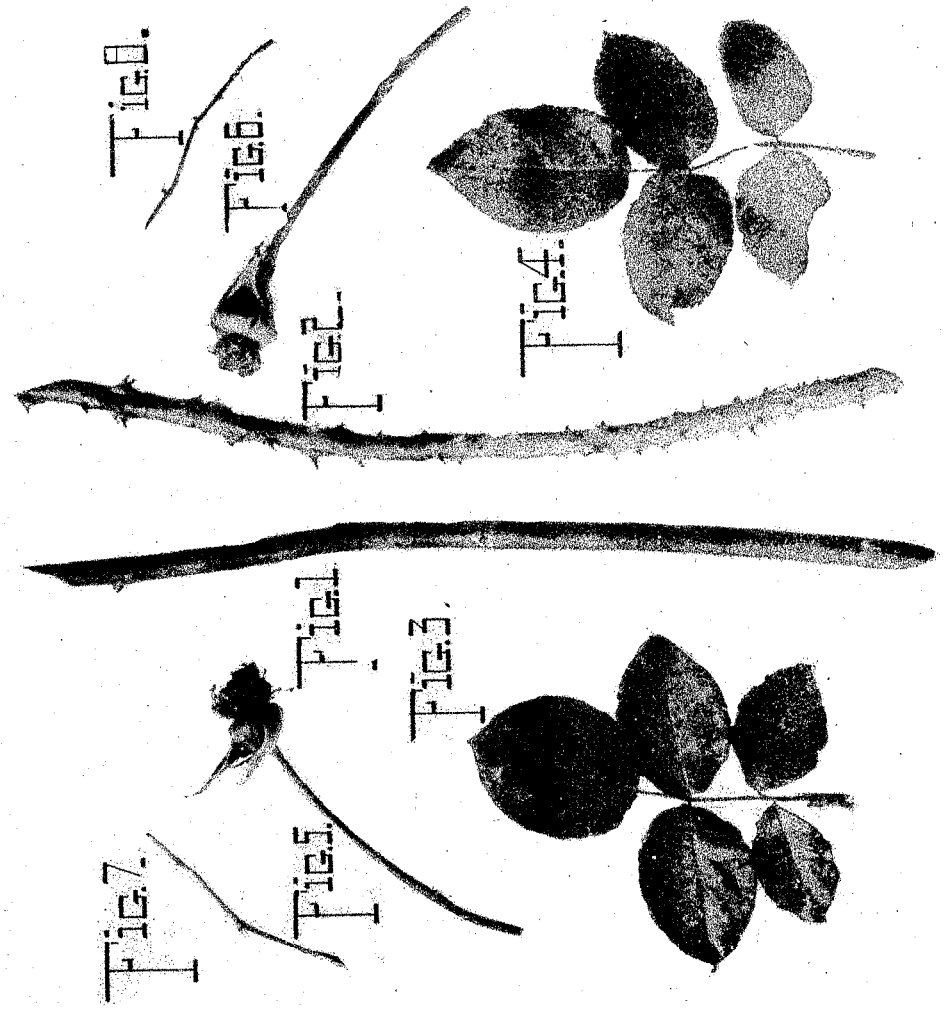
INVENTOR
Lenton Newman
By Robb & Robb
ATTORNEYS Patented Sept. 29, 1942

Plant Pat. 545

UNITED STATES PATENT OFFICE

545

ROSE PLANT

Lenton Newman, Tyler, Tex., assignor to Dixie Rose Nursery, Tyler, Tex.

Application December 22, 1941, Serial No. 424,043

1 Claim. (Cl. 47—61)

The present discovery relates to a new and distinct variety of rose plant, originating as a sport of the well known variety "E. G. Hill" which I found growing upon its parent plant in the vicinity of Tyler, Smith County, Texas.

This new rose attracted my attention because of the fact that while the parent plant has around 50 to 60 thorns and prickles per foot of flowering wood, the sport was thornless. This mutation characteristic alone not only constituted an attractive novelty, but made of it a valuable garden rose as well.

It may be noted that in general, the habit of growth, color and size of the bloom, etc., are very similar to the parent rose, the point of primary difference is the entire absence of thorns, prickles and hairs, as will be apparent in the accompanying illustration. There is another slight difference which warrants consideration and that relates to the leaf edges, which in the parent plant are heavily serrated, while in the new rose the edges are either smooth or very slightly serrated, but otherwise the foliages of the two varieties are practically alike in all respects.

In the accompanying drawing I have illustrated corresponding portions of the two plants, E. G. Hill and this sport for comparison purposes to thereby bring out more clearly the distinctions above referred to.

In said drawing:

Figure 1 shows a representative portion of a stem of the new variety, while Figure 2 is a corresponding specimen of the parent E. G. Hill;

Figures 3 and 4 show similar specimens of the foliage of the new variety and parent, respectively;

Figures 5 and 6 show comparative specimens of the peduncle of each variety in order named above; and Figures 7 and 8 show comparative specimens of the rachis of each in the order named.

The following is a detail description of this new rose, color terminology being in accord with Ridgway's Color Standard and general dictionary meaning:

Type: Hardy; tall; bush; outdoor; sport; for cut flowers and garden decoration.
Class: Hybrid tea.
Parentage: Sport of E. G. Hill.
Propagation: Holds its distinguishing characteristics through succeeding propagations by cuttings, grafting, budding and layering.

*Flower*

Locality where grown: Tyler, Texas.
Flowers borne: Singly two, three, four to stem; in regular, flat cluster; on strong long stems.
Quantity of bloom: Abundant, outdoors.
Continuity: Continuous.
Fragrance: Strong; musk.

Bud:

*Peduncle.*—Medium length; heavy; erect, stiff; medium bronze; entirely smooth.

*Before calyx breaks.*—*Size*—medium. *Form*—Short, ovoid with a conspicuous neck, without foliaceous appendages on the surface of the bud, without foliaceous parts extending beyond the tip of the bud.

*As calyx breaks.*—*Color*—Amaranth Purple with Rivage Green Flame, Plates XII and XVIII respectively.

*As first petal opens.*—*Size*—medium. *Form*—ovoid. *Color*, outside—Tyrian Rose, Plate XII, inside—Tyrian Rose, Plate XII.

*Opening.*—Opens up well.

Bloom:

*Size.*—Large, 3 to 3¼ inches.

*Petalage.*—Double; from fifty-one to sixty arranged regularly.

*Form.*—Cupped at first; becoming flat; petals remaining at first tightly rolled inward; becoming later, at maturity, loosely rolled outward.

Petals: Thick; inside, satiny; outside, shiny.

*Shape.*—Outside—round, with apex flat. Intermediate — round. Inside — ovate; irregular.

This description of a newly opened flower was made from a rose grown outdoors, in the month of October, 1941, at Tyler, Texas:

*Color.*—Outside petal, outside surface—Pomegranate Purple, Plate XII–71–V–RR–*h*. Inside surface—Rose Red, Plate XII–71–V–RR. Intermediate petal, outside surface—Pomegranate Purple, Plate XII–71–V–RR–*i*. Inside surface—Rose Red, Plate XII–71–V–RR. Inner petal, outside surface—Pomegranate Purple, Plate XII–71–V–RR–*i*. Inside surface—Rose Red, Plate XII–71–V–RR.

This description was made from a rose that was open for three days, outdoors in the month of October, 1941, at Tyler, Texas:

*Color.*—Outside petal, outside surface—Tyrian Rose, Plate XII–69–RV–R. Inside surface—Tyrian Rose, Plate XII–69–RV–R. Inside petal, outside surface—Rose Red, Plate XII–71–V–RR–*b*. Inside surface—Rose Red, Plate XII–71–V–RR.

*General color effect.*—Newly opened flower—Rose Red, Plate XII. Three days open—Tyrian Rose, Plate XII.

*Behavior.*—Drop off cleanly.

*Flower longevity.*—On bush in garden, five days in October. Cut roses grown outdoors, four days in October.

*Reproductive organs*

Stamens: Few; arranged irregularly about pistils, mixed with petaloids.

Filaments: Long; reddish; most with anthers.
Anthers: Large; reddish; all open at once.
Pollen: Moderate; yellow.
Pistils: Many.
Styles: Uneven; short; heavy; bunched.
Stigma: Yellow.
Ovaries: Protruding from calyx.
Sepals: Permanent; short; spear-shaped, recurved.
*Color.*—Inside—bronze; outside—light green.

*Plant*

Foliage:
*Leaves.*—Compound of 3, 5 leaflets; normal amount; moderately large; moderately heavy; glossy, wrinkled.
*Leaflets.*—Ovoid with apex acute; base round; margin finely serrate.
*Color.*—*Mature,* upper surface—Normal dark green; under surface—gray. *Young,* upper surface—very bronze red; under surface—bronze.
*Rachis.*—Medium heavy. Upper side—grooved, hairy. Under side—extremely smooth.
*Stipules.*—Medium length; medium wide; with medium points, turning out at an angle of less than 45°.
*Disease.*—Resistant to mildew, blackspot, insofar as this is evidenced by absence of any disease throughout development and establishment of this variety.

Growth:
*Habit.*—Upright; sprawling; much branched.
*Growth.*—Vigorous.
*Canes.*—Medium heavy.
*Main stems.*—Gray-green. *Thorns, prickles, hairs*—none.
*Branches.*—Bright gray-green. *Thorns, prickles, hairs*—none.
*New shoots.*—Dull bronze red. *Thorns, prickles, hairs*—none.

I claim:

A new and distinct variety of rose plant, characterized as to novelty by the absence of thorns, prickles and hairs, and by the smooth to very slightly serrated edges of its leaves, substantially as shown and described.

LENTON NEWMAN.